United States Patent [19]

Bushman

[11] 4,321,156
[45] Mar. 23, 1982

[54] SHAMPOO COMPOSITION

[75] Inventor: Donald W. Bushman, Racine, Wis.

[73] Assignee: S. C. Johnson & Son, Inc., Racine, Wis.

[21] Appl. No.: 36,966

[22] Filed: May 8, 1979

Related U.S. Application Data

[63] Continuation of Ser. No. 782,855, Mar. 30, 1977, abandoned.

[51] Int. Cl.³ .................... A61K 7/06; C11D 1/14; C11D 3/04; C11D 17/08
[52] U.S. Cl. .................... 252/142; 252/136; 252/523; 252/531; 252/532; 252/541; 252/545; 252/550; 252/551; 252/DIG. 13
[58] Field of Search .................... 252/89.1, 136, 142, 252/531, 526, 545, 548, 550, 551, DIG. 13, 541, 523; 424/70

[56] References Cited

U.S. PATENT DOCUMENTS

| | | | |
|---|---|---|---|
| 2,303,932 | 12/1942 | Guild | 252/142 |
| 2,599,665 | 6/1952 | Stephan | 252/142 |
| 3,042,621 | 7/1962 | Kirschenbauer | 252/142 |
| 3,496,110 | 2/1970 | Shumway | 424/70 |
| 3,634,264 | 1/1972 | Pence | 424/70 |
| 3,893,955 | 7/1975 | Hewitt | 252/DIG. 13 |
| 3,996,146 | 12/1977 | Tarasou | 252/142 |

OTHER PUBLICATIONS

Brandau, Robt. P.: "Cosmetic Surfactants in this Detergent Age", *Cosmetics & Toiletries*, 1969.

*Primary Examiner*—Dennis L. Albrecht

[57] ABSTRACT

An improved shampoo composition comprising from 12.5 to 25% by weight of an anionic detergent from 1.0 to 3.5% by weight of an inorganic salt, from 0.25 to 1% by weight of an acid selected from the group consisting of citric acid, boric acid, hydrochloric acid, phosphoric acid, ascorbic acid and mixtures thereof and water, said composition having a viscosity of between 4000 and 15,000 centipoise and a pH of from 3 to 4.5.

3 Claims, No Drawings

SHAMPOO COMPOSITION

This is a continuation of application Ser. No. 782,855, filed Mar. 30, 1977, now abandoned.

BACKGROUND OF THE INVENTION

This invention relates to an acidic shampoo composition. More particularly this invention relates to an acidic shampoo composition having improved cleaning.

Acid side shampoos, i.e. shampoos with a pH of less than seven have been known and in fact there are a number of shampoos currently on the market having a pH within the range of 5 to 7. It is known that high alkaline shampoos tend to damage hair and accordingly there has been a recent switch towards shampoo compositions which are less alkaline.

U.S. Pat. Nos. 2,289,004, 2,303,932, 2,599,665 and 2,892,756 describe acid side shampoo hair treating compositions. These patents describe compositions having pHs with the range of from 2 to 7 and indicate that damage to the hair can be minimized by using a shampoo having a pH near the isoelectric point of hair, i.e. pH 4.5.

Also there are a number of patents and publications which describe the use of anionic detergents as the cleaning agent in the shampoo composition. The most commonly used anionic detergent is sodium lauryl sulfate. This detergent is an effective cleaner for the hair and has reasonable solubility.

It has been found that an improved cleaning shampoo composition can be prepared by incorporating 12.5 to 25% by weight of an anionic detergent selected from the group consisting of M-lauryl sulfate, mixtures of M-lauryl sulfate and M-lauryl sulfate plus from 1 to 10 moles of ethyleneoxide and mixtures of M-lauryl sulfate and triethanolamine lauryl sulfate wherein M is selected from sodium, potassium and ammonium, from 1.0 to 3.5% by weight of an inorganic salt soluble in the composition and from 0.25 to 1% by weight of an acid selected from citric acid, boric acid, hydrochloric acid, phosphoric acid, ascorbic acid and mixtures thereof, the composition having a pH within the range of 3 to 4.5 and a viscosity within the range of from 4000 to 15,000 centipoise.

It is surprisingly found that the composition having an increased viscosity performs significantly better than a similar composition having a lower viscosity and that compositions having lower pHs perform better than compositions having higher pHs, furthermore the compositions having lower pH and higher viscosity perform better than the similar compositions having either higher pH or lower viscosity. The improvement in performance appears to be synergistic since the combined effects of increased viscosity and descreased pH are exceeded by the composition having increased viscosity and decreased pH.

DETAILED DESCRIPTION OF THE INVENTION

The prime cleaning component of the composition of the present invention is the anionic detergent. Anionic detergents useful in the present invention are selected from the group of M-lauryl sulfate, mixtures of M-lauryl sulfate and M-lauryl sulfate plus 1 to 10 moles of ethyleneoxide and mixtures of M-lauryl sulfate and triethanolamine lauryl sulfate wherein M is selected from sodium, potassium and ammonium. The total anionic detergent present in the composition in the present invention should be within the range of from 12.5 to 25% by weight and particularly within the range from 14 to 21% by weight anionic detergent. When mixtures of M-lauryl sulfate are used with the other anionic detergents as described above, the mixture should be within the range of from 0 to 9 parts other anionic detergent per 1 part M-lauryl sulfate. The preferred M-lauryl sulfate for use in the composition of the present invention is ammonium lauryl sulfate.

The second component of the composition of the present invention is an inorganic salt. The primary function of the inorganic salt is to provide free electrolyte which increases the viscosity of the composition. Within a certain range of inorganic salts, the viscosity of the composition increases, however, above or below the range, i.e. from 1.0 to 3.5% by weight, the viscosity of the resultant shampoo composition decreases. It is within this maximum range of viscosity that the performance properties of the shampoo are most surprising. Any non-toxic inorganic salt which is soluble in the composition of the present invention is suitable such as sodium chloride, potassium chloride, lithium chloride, ammonium chloride, sodium citrate, potassium citrate, lithium citrate and ammonium citrate. The preferred inorganic salts are ammonium chloride, sodium chloride and potassium chloride. The most preferred salt is ammonium chloride. As noted above, these salts may be present in a range of from 1.0 to 3.5% and is preferred that the salt be present in the range of about 1.4 to 2.75% by weight of the total composition.

The viscosity of the composition should be within the range of 4000 to 15,000 centipoise and preferably within the range of 5000 to 10,000 centipoise. The viscosity is measured using a Brookfield viscometer equipped with a number LV4 spindle set at 30 RPM.

The third component of the present invention is an acidifying agent. The prime purpose of these acidifying or pH control agents is to lower the pH of the resultant composition. Although any suitable acid can be utilized to control the pH of the composition it has been found particularly acceptible to use the following acids: citric acid, boric acid, hydrochloric acid, phosphoric acid, ascorbic acid and mixtures. These acids tend to have a buffering effect within the desired pH range when used in combination with the lauryl sulfate anionic detergent and the inorganic salt. Although the exact amount of the acid added is not critical, it is important to add sufficient acid to the composition so that the pH is maintained within the range of from 3 to 4.5 and preferably within the range of 3.3–4.0. Generally from 0.25 to 1% by weight is satisfactory.

The bulk of the composition of the present invention comprises water. Substantially any water can be utilized in the composition although good manufacturing procedures require that the water be deionized and substantially free of major contaminants and impurities.

In addition to the above noted ingredients compositions of the present invention can include a number of other conventional additives including dyes, pigments, pearlessing agents, perfumes, preservatives and the like. These ingredients should be present in the composition preferably in combined amounts of less than 5% and in individual amounts of less than 2% each.

The composition of the present invention will now be illustrated by way of the following examples which are for the purpose of illustration only and are in no way to be considered as limiting.

EXAMPLE I

A shampoo composition having the following composition was prepared: ammonium lauryl sulfate (28%) 60%, ammonium chloride 2.5%, citric acid 0.35%, fragrance 0.5%, formalin 0.134%, color QS, deionized water to 100%. The composition as prepared had a pH of 3.65 and a viscosity of 10,000.

COMPARATIVE EXAMPLES I, II AND III

Compositions similar to the composition in Example I were prepared with the exception that the level of citric acid and ammonium chloride was varied as shown in Table 1.

TABLE I

| Example | Citric Acid | $NH_4Cl$ | pH | Visc | ΔL |
| --- | --- | --- | --- | --- | --- |
| 1 | 0.35 | 2.5 | 3.65 | 10,200 | 254 |
| Comparative Ex. 1 | — | 0.5 | 6.0 | 29 | 180 |
| Comparative Ex. 2 | — | 2.5 | 5.6 | 10,800 | 199 |
| Comparative Ex. 3 | 0.35 | 0.5 | 3.7 | 45 | 220 |

The compositions of the comparative Examples I, II and III and Example I were all tested on about 30 women in half head tests comparing 2 different formulations. The composition of Example I was preferred over each of the comparative examples. Furthermore, each of these compositions was tested in a Terg-O-Tometer for cleaning. The cleaning scores ΔL for Example I were higher than the cleaning scores from comparative examples I, II and III and the improvement in cleaning from comparative example I to Example I is greater than the combined increase from comparative Example I of comparative Examples II and III.

EXAMPLES 2-4

The following shampoo formulations were prepared:

| | Example 2 | Example 3 | Example 4 |
| --- | --- | --- | --- |
| Ammonium Lauryl Sulfate (28%) | 50.0 | 60.0 | 75.0 |
| Ammonium Chloride | 2.75 | 2.0 | 1.4 |
| Citric Acid | 0.35 | 0.35 | 0.35 |
| Color | qs | qs | qs |
| Fragrance | qs | qs | qs |
| Formalin | qs | qs | qs |
| D. I. Water | qs | qs | qs |
| | 100.0 | 100.0 | 100.0 |
| pH | 3.6 | 3.6 | 3.6 |
| Viscosity | 6000 | 6000 | 6000 |

Each of the above formula performed in a manner similar to the formula of Example 1.

What I claim is:

1. A shampoo composition consisting essentially of from 14 to 21% by weight of an anionic detergent selected from the group consisting of ammonium lauryl sulfate and mixtures of ammonium lauryl sulfate with ammonium lauryl sulfate plus 1 to 10 moles of ethylene oxide, wherein the mixtures are within the range of from 0 to 9 parts ammonium lauryl sulfate plus 1 to 10 moles of ethylene oxide to one part ammonium lauryl sulfate; from 0.25 to 1% by weight citric acid; from 1.4 to 2.75% by weight of ammonium chloride and water; the composition having a pH within the range of from 3.0 to 4.0 and a viscosity of from 5,000 to 10,000 centipoise.

2. The shampoo composition of claim 1 wherein said detergent is ammonium lauryl sulfate.

3. The shampoo composition of claim 1 having the following composition: ammonium lauryl sulfate 14–21% by weight, ammonium chloride 1.4–2.75% by weight, citric acid 0.35% by weight and water to 100% having a pH within the range of 3.3 to 4.0 and a viscosity of 5,000 to 10,000 centipoise.

* * * * *